United States Patent [19]

Broome et al.

[11] Patent Number: 5,377,047
[45] Date of Patent: Dec. 27, 1994

[54] DISPOSABLE ENDOSCOPE EMPLOYING POSITIVE AND NEGATIVE GRADIENT INDEX OF REFRACTION OPTICAL MATERIALS

[75] Inventors: Barry G. Broome, Glendora, Calif.; John E. Anderson, Blacksburg, Va.; Richard W. Mott, Seminole, Fla.

[73] Assignee: Linvatec Corporation, Largo, Fla.

[21] Appl. No.: 868,055

[22] Filed: Apr. 13, 1992

[51] Int. Cl.⁵ .............................. G02B 9/00
[52] U.S. Cl. .................... 359/654; 359/362; 359/652
[58] Field of Search .............. 359/642, 435, 652-656, 359/708, 262; 358/98

[56] References Cited

U.S. PATENT DOCUMENTS

| | | | |
|---|---|---|---|
| 4,515,444 | 5/1985 | Prescott et al. | 359/654 |
| 4,639,094 | 1/1987 | Aono | 359/654 |
| 4,641,927 | 2/1987 | Prescott et al. | 359/654 |
| 4,723,843 | 2/1988 | Zobel | 359/435 |
| 4,734,491 | 4/1988 | Takahashi | 359/652 |
| 4,755,029 | 7/1988 | Okabe | 359/661 |
| 4,762,403 | 8/1988 | Hattori | 359/654 |
| 4,783,154 | 11/1988 | Takahashi | 359/652 |
| 4,838,247 | 6/1989 | Forkner | 128/6 |
| 4,859,040 | 8/1989 | Kitagishi et al. | 359/652 |
| 4,895,433 | 1/1990 | Takahashi et al. | 359/654 |
| 4,930,880 | 6/1990 | Miyauchi | 359/652 |
| 5,093,719 | 3/1992 | Prescott | 358/98 |
| 5,117,308 | 5/1992 | Tsuchida et al. | 359/654 |
| 5,191,203 | 3/1993 | McKinley | 359/652 |

FOREIGN PATENT DOCUMENTS

| | | | |
|---|---|---|---|
| 99413 | 6/1984 | Japan | 359/654 |
| 1277496 | 6/1972 | United Kingdom | |

*Primary Examiner*—Loha Ben
*Assistant Examiner*—Thong Nguyen

[57] ABSTRACT

An endoscope including a disposable probe and a non-disposable focusing ocular. The probe comprises negative and positive gradient index of refraction objective elements and a transfer module.

1 Claim, 1 Drawing Sheet

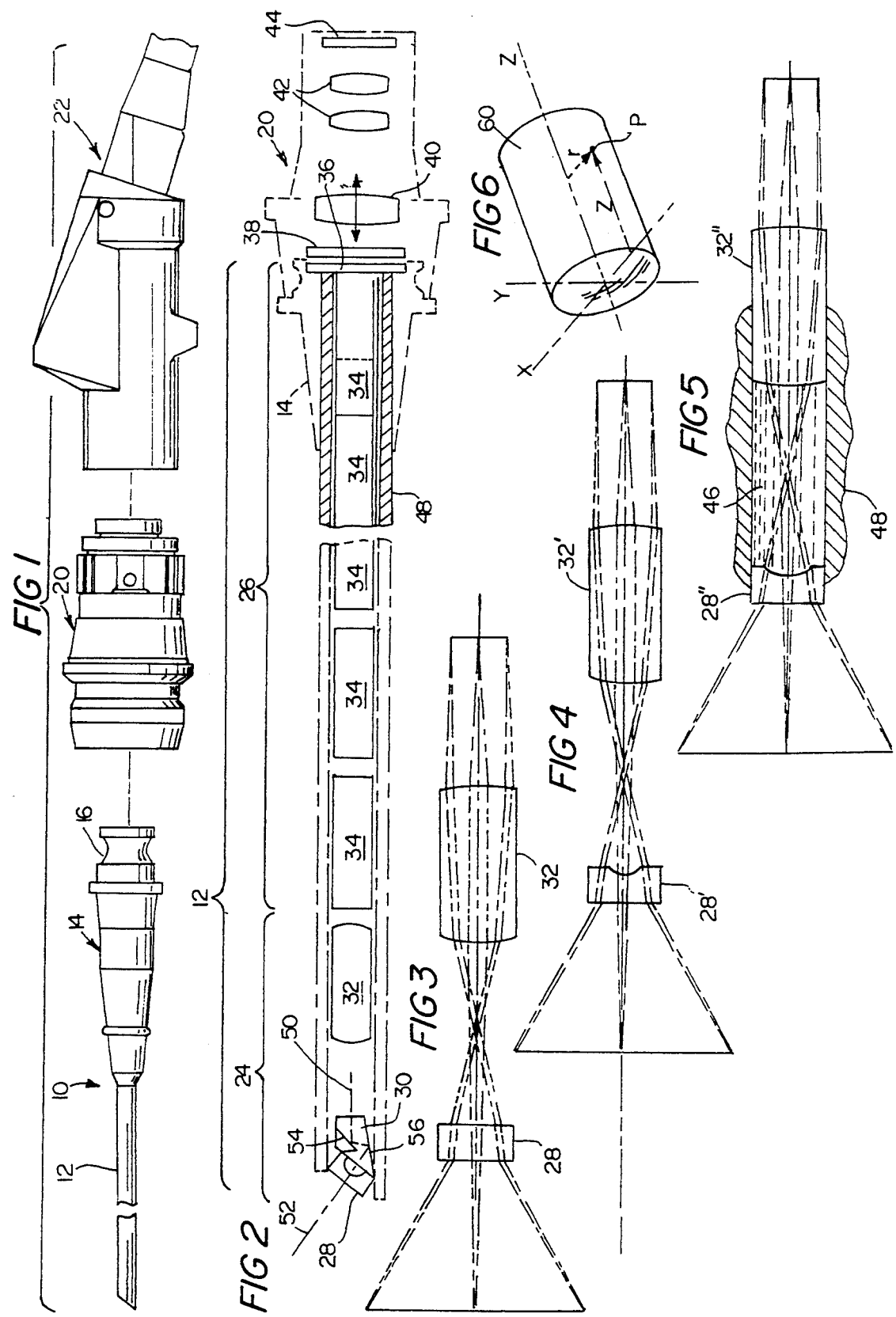

DISPOSABLE ENDOSCOPE EMPLOYING POSITIVE AND NEGATIVE GRADIENT INDEX OF REFRACTION OPTICAL MATERIALS

BACKGROUND OF THE INVENTION

1. Field of the Invention

This invention relates to an imaging endoscope employing gradient index of refraction optical materials in its objective, and, in certain embodiments, in its transfer module. The endoscope of this invention can be manufactured at sufficiently low cost to be cost-effective for single-patient, disposable applications

2. Description of the Prior Art

Substantial benefits are available by performance of endoscopic surgical procedures rather than conventional "open" surgical procedures. More particularly, in an endoscopic surgical procedure the surgeon views the body joint, organ, or other structure to be examined through an elongated optical instrument referred to as an endoscope inserted through a relatively small incision, and performs whatever procedure is deemed necessary using a similarly elongated instrument (also typically referred to as an endoscope) inserted through the same or another small incision. By using these techniques, a majority of the trauma associated with traditional "open" surgery, involving much larger incisions and dissection of obscuring structures, is avoided. The result is substantially reduced health care costs and patient recovery time. For these reasons the use of endoscopic surgical techniques is increasing rapidly.

As used hereinafter, the term "endoscope" refers to an imaging endoscope, that is, an elongated optical instrument through which a surgeon views the surgical site. In general, an endoscope includes an objective at the distal tip of the endoscope for forming the image of the surgical site, an ocular which may include an eyepiece for direct viewing or may present the image to a video camera for displaying a video image of the site, and an elongated transfer module for transferring the image from the objective to the ocular. The objective may also include a prism if it is desired that the center of the field of view of the endoscope be at an oblique angle to the optical axis of the elongated probe.

Conventional endoscopes involve complex optical designs including a large number of glass elements, and are relatively difficult to fully sterilize. This is a particular problem given the present increased fear of infection. Further, many conventional endoscopes are relatively fragile and are expensive to repair. Accordingly, there is a substantial need in the art for a disposable endoscope satisfactory for forming an image of a surgical site of interest that is manufacturable at low cost so as to be cost-effective for single-patient, disposable applications.

The prior art has attempted to provide disposable endoscopes. In general, however, the cost of the conventional glass optical elements employed, typically having numerous individually polished spherical optical surfaces, has been so high as to render these instruments too expensive for single-patient, disposable use.

The prior art has suggested processes for forming aspheric optical surfaces on glass elements, in order to limit the number of individual glass elements required. To date no cost-effective process is available for doing so. To overcome the cost of glass optical elements, and also to overcome the limitation to spherical optical surfaces, the prior art has suggested employment of plastic optical elements that may readily be molded with aspheric surfaces where necessary. However, again the prior art has not to date provided an optically satisfactory endoscope manufacturable in a cost-effective fashion for single-patient, disposable use.

In further attempts to overcome these limitations, the art has also proposed manufacture of endoscopes using optical materials having a gradient in the index of refraction. Such "GRIN" materials are well characterized and are being employed in increasing numbers of optical devices.

The basic technique for forming GRIN materials is to diffuse atoms of elements altering the index of refraction of glass into the glass under appropriate conditions of temperature and pressure. With respect to generally cylindrical optical elements, the prior art suggests both "axial GRIN" materials wherein the index of refraction varies axially, that is, along the optical axis of an individual optical element, and also "radial GRIN" materials, that is, wherein the index of refraction is higher along the optical axis than at the radial periphery of the element, or vice versa. The variation in index of refraction for both axial and radial GRIN materials is symmetric about the optical axis. Radial GRIN optical elements in which the index of refraction is higher at the optical axis than at the radial periphery are referred to as having a positive gradient index of refraction, or "positive GRIN", while those having a higher index of refraction at the periphery than at the optical axis are termed "negative GRIN".

While as indicated axial and both positive and negative radial GRIN materials are suggested by the art for use in various optical instruments, in fact axial GRIN materials are not commonly employed in the design of optical instruments. Moreover, referring to radial GRIN elements, it is substantially more difficult to manufacture negative GRIN elements than positive GRIN elements. At the present time, only positive GRIN elements are manufactured in any significant quantity. Those of skill in the art will recognize accordingly that when a GRIN element is mentioned in the prior art without further description, it may be safely assumed that a positive radial GRIN element is intended.

With respect to specific discussion of the use of GRIN materials for endoscopes, U.S. Pat. No. 4,515,444 to Prescott et al teaches the employment of GRIN rod lenses with a spacer rod of a homogeneous (that is, non-GRIN) material between the objective and the transfer module of an endoscope. Prescott et al suggests that the GRIN rod lenses sold under the trade name "SELFOC" by Nippon Sheet Glass Co. of Japan can be employed for this purpose. U.S. Pat. No. 4,641,927 also to Prescott et al again teaches the use of GRIN rod lenses with a homogeneous lens following a transfer module of an endoscope to provide chromatic aberration correction, and additionally teaches that a GRIN element can be employed as an objective lens.

U.S. Pat. No. 4,723,843 to Zobel suggests that it is advantageous to use a plurality of relatively short GRIN lenses for a transfer module of an endoscope, rather than a single elongated GRIN rod lens, to reduce breakage. Images of the object are formed at the center of each of the elements of the transfer module.

U.S. Pat. No. 4,735,491 to Takahashi indicates that it is known to use the so-called "SELFOC" GRIN rod lenses for both the objective and the elements of the transfer module of an endoscope, but indicates that to do so leads to high chromatic aberration and additional image degradation. The specific improvement proposed by Takahashi is to employ a homogeneous distal objective lens, using the GRIN materials only for the lenses of the transfer module such that chromatic aberrations are reduced, and to make one of these axially movable together with one of the objective lenses for focus adjustment.

U.S. Pat. No. 4,755,029 to Okabe indicates that it is conventional to use a plano-ended GRIN rod lens as a distal objective lens for an endoscope, that is, at the tip of the endoscope. The specific improvement proposed by Okabe is to employ a distal GRIN objective lens having either a planar or a convex distal surface, and a convex proximal surface. Okabe provides an aperture stop outside the distal objective lens and suggests that a fiber optic bundle can be employed as a transfer module.

U.S. Pat. No. 4,783,154 to Takahashi states that it is conventional to use a GRIN rod-like lens in a transfer module of an endoscope. The invention proposed by Takahashi involves employment of homogeneous rod-like lens components in the transfer module, each associated with a GRIN lens. The GRIN lenses may be plano-concave, concave-convex or concave-concave.

U.S. Pat. No. 4,838,247 to Forkner teaches that it is generally conventional to employ GRIN lenses as elements of a transfer module of an imaging endoscope.

U.S. Pat. No. 4,895,433 to Takahashi teaches the use of a GRIN material for the prism of an endoscope, such that the field of view of the endoscope is centered about an axis at an angle to the optical axis of the probe, as well as use of GRIN materials for other optical elements of the objective. Takahashi's GRIN prism is neither "axial GRIN" or "radial GRIN" as these terms were defined above, as the variation in refractive index is not symmetric about the optical axis. Rather, the index of refraction varies linearly transversely across the prism, the gradient being at an angle to the optical axis. In at least one embodiment (see FIGS. 15A and 15B, column 7, lines 30–53), Takahashi suggests integral formation of the prism with a plano-concave element, such that both exhibit the same variation in index of refraction. Takahashi suggests that a fiber optic bundle should be employed as the transfer module.

Among other prior art documents not specifically directed to designs of endoscopes employing GRIN materials, U.S. Pat. No. 4,930,880 to Miyauchi teaches that in general an "axial GRIN" lens, in which the index of refraction varies axially rather than radially, and having a spherical optical surface, can be equivalent to an aspheric lens of a homogeneous, that is, non-GRIN material. Miyauchi does not discuss the application of this broad principle to design of an endoscope.

U.S. Pat. No. 4,859,040 to Kitagishi et al teaches several embodiments of telephoto and zoom lenses using elements formed of both positive and negative radial GRIN materials, including materials exhibiting both axial and radial GRIN characteristics. Kitagishi et al state at col. 11, lines 13–15 that the invention disclosed "may be applied to observation systems or illumination systems of microscope, telescope or others".

Finally, U.K. Patent No. 1,277,496 of Nippon Selfoc Kabushiki Kaisha discusses the manufacture of positive and negative radial GRIN materials of transparent polymeric resins. As noted above, GRIN materials may also be made of glasses having materials which alter the index of refraction diffused into the glass during manufacture.

However, despite the presence in the prior art of various suggestions for the use of GRIN optical elements for various optical instruments, and specifically for endoscopes, there has as yet been provided no imaging endoscope manufacturable sufficiently inexpensively as to be cost-effective for single-patient, disposable applications.

SUMMARY OF THE INVENTION

It is therefore an object of the invention to provide an endoscope manufacturable at sufficiently low cost to be cost-effective for single-patient, disposable use and providing optical performance at least equivalent to that of relatively fragile conventional endoscopes requiring sterilization.

These and other objects of the invention, appearing as the discussion thereof below proceeds, are satisfied by the present invention.

According to the present invention, an objective assembly for an endoscope comprises a distal field-widening objective element of a negative GRIN material, that is, having a higher index of refraction at the radial periphery of the element than at its center, and a positive GRIN proximal image-forming objective element. In certain embodiments of the invention, all optical surfaces of both distal and proximal objective elements may be planar; in others, the distal objective element is plano-concave and the optical surfaces of the proximal element may be convex. The axial space between the distal and proximal elements may be filled with an optical liquid such as immersion oil. A prism may be interposed between the distal and proximal elements to cause the field of view of the instrument to be angled with respect to the optical axis of the remainder of the probe. The transfer module may comprise a rod and lens construction, GRIN rod elements, or a fiber optic bundle.

In the preferred embodiment the endoscope of the invention comprises a non-disposable focusing ocular and a disposable probe. The disposable probe includes the objective, including the prism if used, and the transfer module. Each of these elements are made sufficiently inexpensively as to be cost-effective for single-patient, disposable use, while the focusing ocular is relatively more expensive and is not disposable.

Other objects and advantages of the present invention will become apparent from the following description of the preferred embodiment taken in conjunction with the accompanying drawings wherein like parts in each of the several figures are identified by the same reference characters.

BRIEF DESCRIPTION OF THE DRAWINGS

FIG. 1 is an exploded view of an endoscope according to the present invention, together with a video camera for displaying a visible image;

FIG. 2 is a broken cross-section of an endoscope according to the present invention;

FIG. 3 is a detailed optical diagram of the objective of the endoscope of the present invention, in a first embodiment thereof;

FIG. 4 is a view similar to FIG. 3 of a second embodiment of the objective of the endoscope of the present invention;

FIG. 5 is a view similar to FIG. 4 of a third embodiment of the objective of the endoscope of the present invention; and FIG. 6 is a diagram explaining the terminology employed to define the variation in refractive index of the materials used in an exemplary embodiment of the invention.

DESCRIPTION OF THE PREFERRED EMBODIMENTS

AS shown in FIG. 1, the endoscope according to the invention includes a disposable portion 10, including an elongated probe 12 and a terminal portion 14, and a focusing ocular 20. In the preferred embodiment of the invention the focusing ocular 20 is not disposable. The terminal portion 14 of the disposable probe 10 further includes a male member 16 received in a recess formed in the body of the focusing ocular 20. The disposable probe 12 includes an objective assembly 24 (see FIG. 2) at its distal tip, forming an image of an object juxtaposed to the tip of the probe 12, and a transfer module 26 for transferring the image formed by the objective to the focusing ocular 20. The ocular 20 may include an eyepiece; more commonly, the ocular 20 transfers the image to a video camera 22 for forming a visible image of the object. The ocular 20, and specifically its assembly to the probe 12 and to the video camera 22, may be generally in accordance with the teachings of the prior art, for example, as embodied in the IntraVision Arthroscopic System manufactured by the Concept Division of Linvatec Corporation, Largo, Fla.

The objective assembly 24 includes a first distal field-widening optical element 28, an optional prism 30, and a proximal image-forming optical element 32. The transfer module includes a number of substantially identical GRIN rod lenses 34, and is terminated by window 36. The focusing ocular 20 includes a mating window 38 and a plurality of lenses 40, 42 for providing the image to the video camera 22. One lens 40 may be axially movable to allow focusing of images of objects at various distances from the tip of the probe 12. The focusing ocular 20 may be terminated by a further window 44 mating with a similar window (not shown) comprised by the video camera 22 or other image forming device. The optical elements of the probe 12 are cylindrical and are aligned conveniently along an optical axis 50 of the probe 10 by disposition in an elongated metallic tube 48. A prism 30 may be used to introduce an angle between the axis 52 of the field of view and the optical axis 50 of the probe 12.

FIGS. 3, 4 and 5 show different embodiments of the distal optical element 28 and proximal optical element 32 of the objective according to the present invention. These elements vary in each of these three embodiments; accordingly, the distal element is numbered 28 in the FIG. 3 embodiment, 28' in the FIG. 4 embodiment and 28" in the FIG. 5 embodiment. The proximal optical element is numbered 32, 32', and 32" correspondingly. It is possible if desired to dispose a prism 30 between the proximal and distal elements 28 and 32 in each of the embodiments of the objective shown in FIGS. 3, 4 and 5; the prism 30 is omitted for clarity of the view.

In each embodiment of the objective shown, the distal field-widening optical element 28, 28', 28" comprises a negative GRIN material, that is, a material having a higher index of refraction at its periphery than at the optical axis, and each of the proximal image-forming elements 32, 32', 32" comprises a positive GRIN material, that is, a material having a higher index of refraction at the optical axis than at its periphery. However the invention is not necessarily so limited; a positive GRIN distal element may be employed together with a negative GRIN proximal element. Use of elements of both positive and negative GRIN materials in the objective of the invention substantially corrects for chromatic aberration. Each of the embodiments of the objective shown includes a negative GRIN distal element and a positive GRIN proximal element. As the refractive index of the distal element 28 is higher on the periphery thereof than along the optical axis thereof, rays of light are bent more at the periphery than along the optical axis, effectively further widening the field of view of the endoscope. Employment of the positive GRIN material for the proximal element 32 focuses light rays in the manner of a biconvex lens.

In the embodiment of FIG. 3 the four optical surfaces of the distal element 28 and the proximal element 32 are all plano, i.e., optically flat and perpendicular to the optical axis. Such plano-surfaced elements are less expensive to manufacture than curved-surfaced elements, but have comparatively reduced optical power. In the embodiment shown in FIG. 4, distal element 28' is plano-concave, that is, has a concave proximal surface. The plano-concave element 28' has greater field-widening power than the plano element 28. In the same embodiment it is desirable that the optical surfaces of the proximal element 32' be convex as shown to enhance the image-forming power of the positive GRIN material.

In the further embodiment shown in FIG. 5, the distal element 28" may be plano-concave as is distal element 28' of the FIG. 4 embodiment. Proximal element 32" is also generally of the same configuration as the corresponding element 32', that is, both its proximal and distal optical surfaces are convex. The difference in reference characters indicates that the exact optical specifications of these elements need not be identical in both embodiments. The axial space between the distal and proximal elements 28" and 32" is filled with an optically transparent liquid 46, e.g. an optical immersion oil. The higher refractive index of the oil compared to air allows an increase of the amount of curvature of the optical surfaces of the distal and proximal elements, 28" and 32" respectively, to achieve better aberration correction for a given optical power. The oil assists in correction of chromatic aberration and prevents fogging of the surface of the lenses contacted by the oil. Oil may also be useful in the embodiment of FIG. 3, that is, between plano-surfaced distal and proximal elements 28 and 30. The oil 46 is contained within tubular probe housing 48.

As mentioned above, transfer module 26 may include a bundle of optical fibers, conventional glass elements, a mixture of glass and plastic elements, or rod-like lenses 34 exhibiting GRIN characteristics, as shown. The prior art provides examples of transfer modules of each of these enumerated types. In the event the elements 34 are of GRIN materials, they exhibit positive GRIN. Another useful alternative is to employ a transfer module including a number of identical glass rods having plano ends, thus being relatively inexpensive to manufacture, coupled with paired molded plastic elements having one or more aspheric surfaces.

As discussed above, a prism 30 can be disposed between the distal element 28 and the proximal element 32 of any of the objectives of FIGS. 3 through 5. In order to reduce the cost of the probe, preferably the prism 30 is a generally cylindrical element of optically transparent molded plastic having two reflecting surfaces 54 and 56 inclined with respect to the optical axis 50 of the probe, such that the field of view 52 of the probe 12 is angled with respect to the optical axis of the probe 12. This has the effect of broadening the field of view of the endoscope, allowing the surgeon to see different portions of an interior body cavity by rotating the probe.

If a prism 30 is desired to be added to an embodiment of the objective 24 wherein a transparent oil fills the volume between the proximal and distal elements 28″ and 32″, oil may be disposed in either or both of the volumes between the distal element 28″ and the prism 30 and the prism 30 and the proximal element 32″.

The following Table I provides a suitable optical prescription for the distal lens 28′ and the proximal lens 32′ of the objective in FIG. 4 embodiment, that is, wherein the distal element 28′ is plano-concave and the proximal and distal surfaces of the proximal element 32′ are convex, and no liquid is provided therebetween. In this table, surface 1 is the distal plano surface of the distal element 28′; surface 2 is the proximal plano-concave surface thereof; surface 3 corresponds to a field stop (not shown) disposed between the distal element 28′ and the proximal element 32′; surface 4 is the distal convex surface of the proximal element 32′, and surface 5 is the proximal convex surface of element 32′. The object to objective distance is 2 mm and the image plane distance is 3,210 mm. The figures given under the heading 'RADIUS' refer to the radii of the corresponding surfaces, in mm. The figures under 'THICKNESS' refer to the spacing between the corresponding surfaces, also in mm.

The specifications for the materials of the GRIN elements are provided under the headings "Negrin" and "Pogrin", referring to the distal element 28′ and proximal element 32′, respectively. FIG. 6 illustrates the terminology employed to define the variation in refractive index n of an exemplary optical element 60. If the variation in the refractive index of the material is uniform with respect to the optical axis, the refractive index n at any point P in the material is defined as a function of r and z, wherein r is the radial distance from the z-axis (the z-axis normally coinciding with the optical axis of the instrument, as here) to the point P, and z is the axial distance from the x-y plane tangent to one optical surface of the element 60 at the z-axis to the point P. In a true axial GRIN material, there is no variation in n with r; in a true radial GRIN material, as employed for both proximal element 28 and distal element 32 according to the present invention, there is no variation in n with z. In a positive GRIN material, as used for proximal element 32, the sign of the variation in n with increase in r is negative, so that n is greatest at the z-axis. For a negative GRIN material as used for distal element 28, the sign of the variation in n with increasing r is positive, so that n is minimal at the z-axis.

More specifically, the variation in index of refraction for the elements 28′ and 32′ is given in Table I for each of three wavelengths (abbreviated PWL), specifically 656, 588 and 486 mm, in accordance with the following Equation (1):

$$n(r,z) = n_{00} + c_{01}z + c_{02}z^2 + c_{03}z^3 + c_{04}z^4 + c_{10}r^2 + c_{20}r^4 + c_{30}r^6 + c_{40}r^8 \quad (1)$$

in which $n(r,z)$ = refractive index of the material at a point P located a distance r in mm from the optical axis and an elevation z in mm from a plane tangent to one optical surface of the element at the optical axis;

$n_{00}$ = refractive index at $r=0$, $z=0$;

$c_{0i}$ = coefficients of axial variation of refractive index, i.e., variation parallel to the optical axis; and $c_{i0}$ = coefficients of radial variation of refractive index, i.e., variation parallel to the optical axis.

TABLE 1

| SURFACE | RADIUS (mm) | THICKNESS (mm) | MEDIUM | ELEMENT |
|---|---|---|---|---|
| OBJ: | INFINITY | 2.000000 | AIR | |
| 1: | INFINITY | 0.500000 | 'NEGRIN' | 28′ |
| 2: | 1.24839 | 2.224813 | | |
| STO: | INFINITY | 1.387962 | | |
| 4: | 11.48559 | 2.781881 | 'POGRIN' | 32′ |
| 5: | −7.30623 | 3.210405 | | |
| IMG: | INFINITY | 0.000000 | | |

| PWL 'NEGRIN' | 656.00 | 588.00 | 486.00 |
|---|---|---|---|
| $n_{00}$ | 1.504730 | 1.507410 | 1.514000 |
| $c_{10}$ | 0.6934E-01 | 0.6790E-01 | 0.6456E-01 |
| $c_{01} = c_{02} = c_{03} = c_{04} = 0;\ c_{20} = c_{30} = c_{40} = 0$ | | | |
| PWL 'POGRIN' | 656.00 | 588.00 | 486.00 |
| $n_{00}$ | 1.661300 | 1.667200 | 1.682100 |
| $c_{10}$ | −0.6369E-01 | −0.6350E-01 | −0.6298E-01 |
| $c_{01} = c_{02} = c_{03} = c_{04} = 0;\ c_{20} = c_{30} = c_{40} = 0$ | | | |

In example specified by Table 1, there is no axial variation in the refractive index of either element. Hence the coefficients $C_{0i}$ of the $z^i$ terms are all zero. Moreover a single $C_{i0}$ coefficient, $c_{10}$, factored into the $r^2$ term, is sufficient to specify the radial variation of the refractive index in both elements 28′ and 30′ Hence the coefficients $c_{20}$, $c_{30}$ and $c_{40}$ are all zero.

As can be seen from Table I, the three $c_{10}$ coefficients (again each corresponding to light of a particular wavelength) of the 'negrin' material used for distal element 28′ are all positive; hence the $c_{10}r^2$ term of Equation (1) for this material is positive, and the index of refraction of the material increases with radius, i.e., the index of refraction is greater at the periphery of element 28′ than along the optical axis. By comparison, the three $c_{10}$ coefficients of the 'pogrin' material of proximal element 32′ are all negative; accordingly the $c_{10}r^2$ term of Equation (1) for this material is negative, and the index of refraction decreases with radius, i.e. the index of refraction is greatest along the optical axis of element 32′.

Having described preferred and alternative embodiments of a new and improved disposable endoscope, it is believed that other modifications, variations and changes will be suggested to those skilled in the art in view of the teachings set forth herein, it is therefore to be understood that all such variations, modifications and changes are believed to fall with the scope of the present invention as defined by the appended claims.

What is claimed is:

1. An objective for an endoscope comprising distal and proximal optical elements and having distal and proximal optical surfaces symmetrical about an optical axis, said distal element being formed of a material exhibiting a negative radial gradient in its index of refraction, and said proximal element being formed of a material exhibiting a positive radial gradient in its index of refraction, and wherein the radii of the optical surfaces of said distal and proximal elements and the spacings of the optical surfaces thereof from one another are specified by the following optical prescription:

| SURFACE | RADIUS (mm) | THICKNESS (mm) | MEDIUM |
|---|---|---|---|
| OBJ: | INFINITY | 2.000000 | AIR |
| 1: | INFINITY | 0.500000 | "NEGRIN" |
| 2: | 1.24839 | 2.224813 | |
| STO: | INFINITY | 1.387962 | |
| 4: | 11.48559 | 2.781881 | "POGRIN" |
| 5: | −7.30623 | 3.210405 | |
| IMG: | INFINITY | 0.000000 | | in which surfaces 1 and 2 are the distal and proximal optical surfaces of the distal element, respectively, and surfaces 3 and 4 are the distal and proximal optical surfaces of the proximal element, respectively, and wherein the variation of the indices of refraction of the "negrin" and "pogrin" materials of said distal and proximal elements, respectively, are specified by the following values therefor:

| PWL | 656.00 | 588.00 | 486.00 |
|---|---|---|---|
| "NEGRIN" | | | |
| $n_{00}$ | 1.504730 | 1.507410 | 1.514000 |
| $c_{10}$ | 0.6934E-01 | 0.6790E-01 | 0.6456E-01 |
| $c_{01} = c_{02} = c_{03} = c_{04} = 0;\ c_{20} = c_{30} = c_{40} = 0$ | | | |
| PWL | 656.00 | 588.00 | 486.00 |
| "POGRIN" | | | |
| $n_{00}$ | 1.661300 | 1.667200 | 1.682100 |
| $c_{10}$ | −0.6369E-01 | −0.6350E-01 | −0.6298E-01 |
| $c_{01} = c_{02} = c_{03} = c_{04} = 0;\ c_{20} = c_{30} = c_{40} = 0$ | | | | wherein:

PWL refers to the wavelength of light in nm to which a particular specified value for the index of refraction n refers, and the index of refraction n of the material of each of the proximal and distal elements at any point (r,z) therein is specified by the following equation (1)

$$n(r,z) = n_{00} + c_{01}z + c_{02}z^2 + c_{03}z^3 + c_{04}z^4 + c_{10}r^2 + c_{20}r^4 + c_{30}r^6 + c_{40}r^8 \quad (1)$$

in which:

$n(r,z)$ = refractive index of the material at radius r in mm from the optical axis and elevation z in mm from a plane tangent to one optical surface of the element at the optical axis;

$n_{00}$ = refractive index at r=0, z=0;

$c_{0i}$ = coefficient of axial variation of refractive index;

$c_{i0}$ = coefficient of radial variation of refractive index.

* * * * *